United States Patent [19]

Brudermann

[11] Patent Number: 4,621,628
[45] Date of Patent: Nov. 11, 1986

[54] APPARATUS FOR LOCATING TRANSVERSE HOLES OF INTRAMEDULLARY IMPLANTATES

[75] Inventor: Uwe Brudermann, Kiel, Fed. Rep. of Germany

[73] Assignee: ORTOPEDIA GmbH, Kiel, Fed. Rep. of Germany

[21] Appl. No.: 648,015

[22] Filed: Sep. 6, 1984

[30] Foreign Application Priority Data

Sep. 9, 1983 [DE] Fed. Rep. of Germany ....... 3332642

[51] Int. Cl.$^4$ .............................................. A61F 5/04
[52] U.S. Cl. ............................. 128/92 VD; 128/92 R
[58] Field of Search ............. 128/92 EB, 92 E, 92 R, 128/92 BC

[56] References Cited

U.S. PATENT DOCUMENTS

| | | | |
|---|---|---|---|
| 3,367,326 | 2/1968 | Frazier | 128/92 R |
| 3,782,373 | 1/1974 | Smythe | 128/92 EB |
| 3,814,089 | 6/1974 | Deyerle | 128/92 EB |
| 4,281,649 | 8/1981 | Derweduwen | 128/92 BC |
| 4,418,422 | 11/1983 | Richter et al. | 128/92 EB |

FOREIGN PATENT DOCUMENTS

| | | | |
|---|---|---|---|
| 964149 | 3/1975 | Canada | 128/92 EB |
| 1009445 | 4/1983 | U.S.S.R. | 128/92 EB |

Primary Examiner—Gene Mancene
Assistant Examiner—C. W. Shedd
Attorney, Agent, or Firm—John P. White

[57] ABSTRACT

The apparatus serves to locate transverse holes V of intramedullary implantates, especially in the distal end of implanted interlocking nails, in the fracture treatment of bones. The apparatus includes at least one magnet (13, 16) generating an axially symmetrical field, and a magnetic field detection device (8, 9) having an axial reception characteristic, with one of said two directional elements being adapted to be aligned on the axis of the transverse hole (11) to be located. The other one of said two directional elements, e.g. the magnet (13), is freely movable exteriorly, and therefore adapted to be aligned with the axis of the transverse hole. The output signals of the magnetic field detection device (8, 9) are presented on a display device (17) through a signal processing device (15). By relative displacement of the magnet (13) and of the magnetic field detection device (8, 9), the two axes thereof may be made to coincide, which state can be displayed on the display device by a zero point indication.

22 Claims, 3 Drawing Figures

APPARATUS FOR LOCATING TRANSVERSE HOLES OF INTRAMEDULLARY IMPLANTATES

The present invention relates to an apparatus for locating transverse holes of intramedullary implantates in the fracture treatment of bones, especially for locating transverse holes in the distal end (remote from the body) of implanted interlocking nails, and for the coaxial alignment of a drilling device relative to these transverse holes.

Medullary spikes are used for the mutual intramedullary fixation of fragments of the long hollow bones in the fracture treatment thereof. A special construction of such spikes is provided with bores in both proximal, i.e. towards the body, and distal dispositions to extend transverse to the longitudinal axis of the spike, which bores serve to rigidly connect the bone fragments adjacent to the joint, upon insertion of these spikes, to the spike through auxiliary threaded bolts or pins, thereby to positively interlock their mutual positions relative to each other. This is expedient particularly in the case of multiple fractures, fragmental fractures or fractures with defect portions, and when treatment by means of external fixation elements, i.e. elements positioned on the outer side of the extremeties, is not necessary or advisable.

As the medullary canal of the long hollow bones, in general, neither has a constant cross-section along its full length, nor is linear, for the spiking of bones there are normally used spikes of such profile shapes which provide for a more or less definite geometrical matching of the spike with the configuration of the medullary canal when the spike is driven into the bone. The consequent is that these spikes are generally both twisted and bent when they are driven into the bone. Therefore, when the spike is driven in, the exact position of the distal end of the spike —when the latter is driven in from the proximal end in the usual way—cannot be determined precisely from the proximal end.

For the same reason, it cannot be foreseen, either, what exact position the distal holes (bores) of the spike will assume in the process of driving in, and where, accordingly, the holes have to be provided in the distal fragment of the bone in order to connect or lock the fragment to the spike transversely of the axis of the spike or bone with the aid of the abovementioned bolts or pins. However, these holes must be formed in the bone with a high degree of precision to prevent the metallic drilling chips are removed from the spike material at the edges of the transverse holes formed in the spike during the drilling operation. Otherwise, such drilling chips could remain in the intramedullary portion of the bone and thereby greatly affect in a negative sense the process of healing. For the same reason, simultaneous drilling of the distal holes in bone and spike must be avoided.

Various methods and devices are known for locating the distal holes, which are normally known as "distal location instruments". Below, the mode of operation of such instruments will be described briefly:

(1) For locating the proximal holes (bores), a mechanical location or finding instrument is used which is mechanically fixed to the proximal end of the spike. This location instrument includes a drilling jig which with a sufficient degree of precision aligns coaxially with the proximal hole of the spike being spaced only a few centimeters from the proximal end of the spike, even if the spike has suffered from deformation during the driving-in process. Heretofore, all of the conventional attempts to use location instruments operating in accordance with this principle also for locating the distal holes have failed, if they used such spikes which, in accordance with the original demand, were sufficiently resilient to conform themselves to the configuration of the medullary canal in the course of being driven into the bone.

(2) The use of bone spikes of an annular cross-section involves only the risk of bending of the spike, while rotational errors can be virtually avoided. In this instance, therefore, it is sufficient to determine the exact location of the spike end, since the variation of the spacing of the distal holes from the proximal end of the spike owing to the bending that has taken place is so small to be neglectible. To this end, location instruments are known which by means of magnetic coupling detect, and compensate for, the lateral deviation of the spike axis relative to the drilling direction. Here, the depth dimension of the hole to be drilled is insignificant, since the angular errors of the hole axis, as caused by bending of the spike, relative to the drilling axis are rather small. However, a location instrument of this type can be used only for spikes having a circular cross-section. On the other hand, spikes of this shape can conform themselves to the configuration of the medullary canal to a very low degree only, thereby not insignificantly reducing the strength of the system of the spiked bone.

(3) Another possibility consists in using still stiffer spikes than those mentioned above sub (2), but likewise with a circular cross-section. This would provide the advantage that a location instrument operating in accordance with the method explained above sub (1) might be employed, because bending of the spike during the driving-in process could thereby be avoided, too. In this instance, however, the drawbacks mentioned sub (2) become more prominent. Further, it is also of disadvantage that in this case the medullary canal must be enlarged by drilling to a substantially larger extent prior to insertion of the medullary spike, this resulting not only in the abovementioned disadvantages, but also in increased lesion of the bone substance.

(4) In order to avoid the discussed drawbacks, the most common practice is that the desired spikes—regardless of their kind—are initially driven in, and that thereafter the distal holes are located by means of an X-ray apparatus—generally termed image converter. In this case, the approximately point-shaped source of radiation must be positioned precisely in the direction of the extended axis of the distal hole to be located, which can be recognized from the shadows produced by the hole edges, since the circular hole appears on the screen as a circle only when this position is reached. There are already known location instruments which are mechanically connected to the image converter in such a manner that a drilling jig may be attached thereto upon locating the correct position, with the axis of the drilling jig being aligned with the axis of the hole. However, the accurate positioning of the large and heavy image converter is difficult and troublesome, and the fixation of the image converter relative to the spike and the bone is likewise difficult. Furthermore, however, a serious disadvantage of these conventional instruments is the radiation effect on both the medical personnel and the patent during the positioning and fixation of the drilling jig. Finally, the production of the holes in the bone by means of drills used to this end likewise constitutes an inconvenient and uncertain method.

(5) Therefore, location instruments of the last-described type are seldom used in practice; rather, the piercing or puncture point of the hole through the surface of the skin is marked by means of the pointed end of a scalpel placed in the optical path of the image converter, whereupon the image converter is moved away from the field of operation. Subsequently, the scalpel is used for the incision of the soft tissue, a drilling jig is inserted into, and thereafter the hole is formed in the bone as estimated by the eye. However, this most commonly used method at the same time increases the radiation effect on the operator, as compared with the method discussed above sub (4), while also substantially increasing the risk of inaccurate drilling. Then, drilling errors must be tolerated, and re-drilling or re-adjustment is not possible; and, as an inevitable consequence, metallic chips of the spike material enter the medullary canal. Further, a proper fit of the transverse bolts along with the orderly fixation of the bone fragments which depends on such fit, can hardly be obtained.

It is the object of the present invention to provide an apparatus for locating transverse holes (bores) of intramedullary implantates, particularly of the distal holes of interlocking nails, which apparatus permits the fast, convenient and secure placement of the drilling jig in axial alignment with the transverse holes, without involving a radiation effect on the surgeon and the medical personnel.

According to the present invention, this object is solved in that at least a first directional element in the form of a magnet producing a directional field, and a second directional element in the form of a magnetic field detection device with unidirectional reception characteristic are provided; that one of said two directional elements is adapted to be aligned with an excellent or predetermined receive direction to the axis of the transverse hole to be located; that the other directional element is freely movable, and that the output signals of the magnetic field detection device are fed, through a signal processing device, to a display device displaying the relative position of the directional characteristics of said two directional elements to each other. Preferably, the magnetic directional field is oriented in an axially or rotationally symmetrical fashion.

Thus, in the apparatus according to the invention the directional characteristics of the magnetic field and of the magnetic field detection device are used to control the relative positions of the axes of both directional elements through a display device, such that both axes may be brought into congruence with each other by means of this control display. One of said two directional elements is aligned exactly with the axis of the transverse hole, by, for example, mechanical means disposed interiorly of the implantate, while the other, exteriorly disposed directional element may be used for marking the located hole, such as on the skin, or for positioning a drilling jig.

In order to reduce detection errors, the locating process may be effected by two independent detection steps in which two points of the axis of a transverse hole in the implantate are found or located, which clearly define the position of this axis. Hereby, it is expedient that, perhaps, two diferent movable directional elements are provided, one of which is useful, for example, for finding a point on the body surface, and a second one of which is suitable for finding a point directly on the surface of the bone.

Optionally, the pair of directional elements may be formed and arranged such that, in the one instance, the magnetic field detection device is linked to the axis of the transverse hole in the implantate and the magnet is movably positioned exteriorly, and that, in the other instance, the axis of the transverse hole in the implantate is linked to the magnetic field or the magnet, respectively, and the magnetic field detection device is movable exteriorly.

For generating the magnetic field, there may be used, for example, a permanent magnet or even an electromagnet. Expediently, the magnetic field detection device is provided with one or more magnetically controllable semiconductor elements, with the use of Hall elements being particularly advantageous. However, field plates or other elements may be used while obtaining equivalent effects.

The magnetic field detection device may be arranged such that the maximum of its detection sensitivity coincides respectively with the axis linked to its directional characteristic, such that this axis may be determined by finding the signal maximum. In another advantageous embodiment, the magnetic field detection device is linked to the axis of the respective directional element in such a manner that this axis coincides with the minimum of its directional characteristic, such that the location of this axis may be determined by finding the signal minimum. As mentioned above, there may be determined, for example, two successive search points (positions) on the axis of the transverse hole of the implantate, with the first point being the piercing point of this axis through the surface of the skin and at the same time marking the penetration position for the necessary puncture incision through the soft tissue up to the bone, and with the second search point being defined on the surface of the bone after the effected puncture incision. Thus, expediently an annular magnet may be used for generating the magnetic field, which magnet facilitates easy marking of the first search point on the skin surface. Upon insertion of a drilling jig into the puncture incision, another magnet in the form of a magnetic probe may be inserted into this drilling jig, which probe permits to precisely define the second search point on the bone surface.

In an expedient embodiment, the positioning of the one directional element on axis of the transverse hole in the implantate may be rendered possible in that one of the directional elements is mounted to the head of the probe to be inserted into the implantate having a cross-section contour, with the probe head being adapted to be positioned with a reproducible spacing from the accessible end of the implantate. Here, the probe may include an adjustable stop member for positioning the probe head in correspondence with the varying spacing of the transverse hole from the accessible end of the implantate, which spacing, however, is known in each individual instance.

A possible angular deviation of the directional characteristic of the probe relative to the axis of the transverse hole in the implantate may be prevented from occurring when the probe head is conformed to the inner contour of the implantate and adapted to be positioned within the latter, as a guide means, with its directional characteristic lying coaxially to the transverse hole.

Expediently, the signal processing device includes means for zero balancing in order to compensate magnetic stray fields, such as, for example, the earth magnetic field, prior to the start of the detection. As a display device, in most instances there would be used an optical display device, such as the monitor of an image converter, which is anyhow present in the operating theater. Further, there may be used also other optical display devices, and even acoustic signalling devices or signalling devices alarming other sense organs.

Below, the invention is explained in greater detail in one embodiment thereof with reference to the enclosed drawing, wherein.

Figure 1:
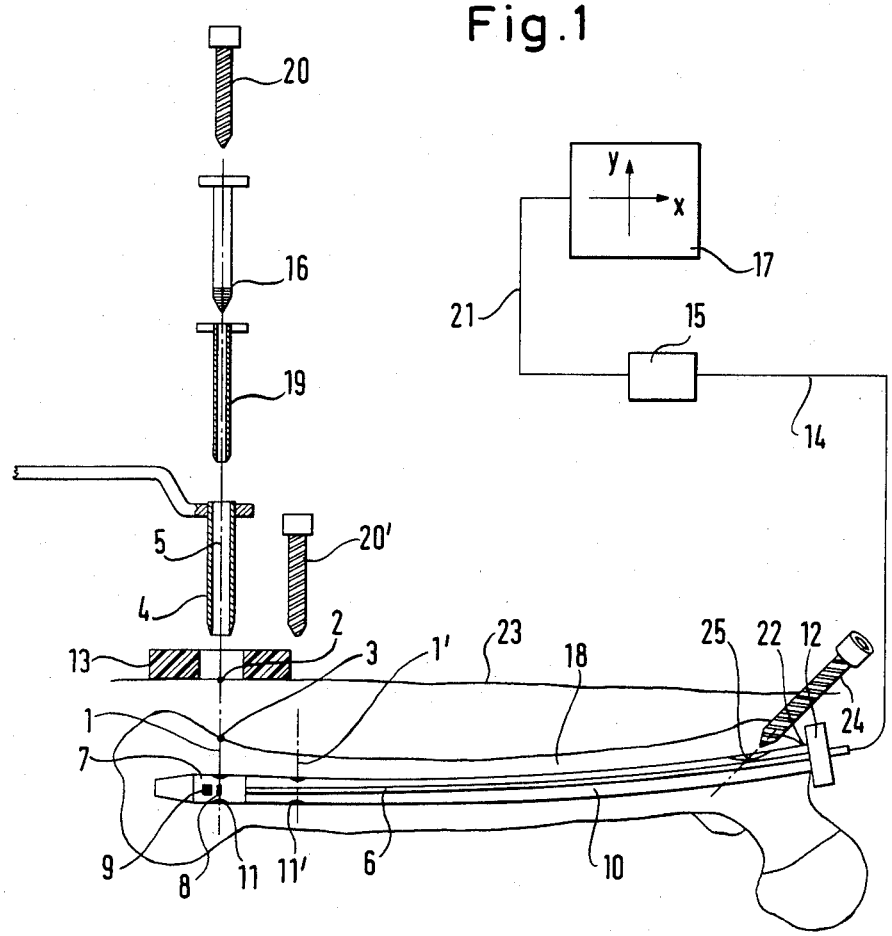
FIG. 1 shows the positioning of an apparatus according to the present invention on an implanted interlocking nail.

FIG. 1 illustrates the positioning of an interlocking nail 10 in the medullary canal of a bone 18 situated with its certain spacing below the skin or body surface 23. In FIG. 1, the spike has been driven into the bone from the right side, and the spike has in the vicinity of its left, i.e. distal, end a pair of transverse holes 11 and 11' for receiving transverse bolts 20 and 20', respectively.

Now, the exact position of the respective drilling axis 1 of a distal hole 11 in the interlocking (medullary) spike 18 is to be determined. This drilling axis may be definitely determined by a linear connecting line of two points 2 and 3 on this axis. In order to place a drilling jig 4 in a position aligned with this axis, the two points 2 and 3 on the drilling axis of the distal hole 11 must be located accordingly, and the axis of the drilling jig must be oriented in accordance with these points, whereupon the hole (bore) may be formed in the bone immediately. The first one (2) of these two points is determined on the skin surface 23, to thereby at the same time define the locus of the puncture incision. The second point 3 is determined on the surface of the outer cortex and, thus, at the same time provides the location on the bone through which the drill must pass. Here, the puncture incision made through the first point 2 and extending up to the bone, sumultaneously receives the drilling jig 4 the axis 5 of which, thus, extends through the initially found point 2.

Figure 2:
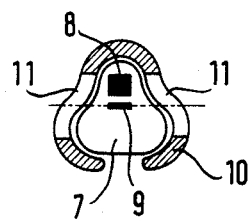
FIG. 2 is a cross-sectional view of an interlocking nail at the level of a transverse hole, with the magnetic field detection device inserted therein.
Figure 3:
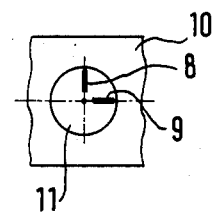
FIG. 3 is a side elevational view of an interlocking nail, as seen in the axial direction of the transverse hole, with the magnetic field detection device inserted therein.

The apparatus according to the invention is used for locating these two points 2 and 3, and this apparatus includes a magnetic field detection device in the form of a probe 6 including a probe head 7 and Hall elements 8 and 9 mounted thereon. Here, these two Hall elements 8 and 9 are mounted in such a manner that their principal planes intersect each other on the axis 1 of the distal hole 11. This axis 1 is the geometrical locus of all points (locations) where an axially symmetrically applied magnetic field does not generate any output signals on both Hall elements. This is achieved in that the probe head 7, as shown in FIG. 2, is formed as a shaped part conformed to the inner contour of the spike 10; accordingly, this probe head, during insertion of the probe 6, is guided in the interior of the, here trifoliate, cross-section of the spike 10, even if the spike 10 during driving in thereof has suffered from bending and/or twisting of some realistic kind. The exact orientation of the probe head 7 or of the Hall generators 8 and 9 in the longitudinal direction of the spike 10 relative to the axis of the transverse hole 11 is obtained by the fact that the spacing of the transverse hole 11 from the proximal end 22 of the spike 10, with a realistically pronounced deformation and in consideration of the elastic deformability of the probe 6 in the shank thereof, is maintained with a sufficient degree of accuracy. For varying lengths of spikes or for the various distal holes 11 or 11' of the spike 10, a stop member 12 may be positioned and fixed on the probe shank 6 in correspondingly different positions prior to inserting the spike into the bone. Corresondingly differently shaped probe heads 7 are required for different spike diameters or different profile (cross-sectional) shapes of the spike, respectively.

The illustrated apparatus further comprises a search magnet in the form of an annular magnet 13, and a bar magnet 16. For forming the hole (bore), the above described drilling jig 4 in combination with an auxiliary insert 19 is used.

The output signals of the Hall elements 8 and 9 are led through a line 14 to a signal processing device 15 by which the Hall elements are also supplied with electric power in the customary manner. The output signals of the processing device 15 are fed through a line 21 to a display device 17 on which, then, the respective relative positions of the axes of the magnetic field detection device on the one hand and of the respectively employed magnet 13 or 16 on the other hand are visualized.

Prior to starting the detection, balancing of the display is necessary. To this end, the search magnets 13 and 16 must be held remote from the assembly such that the zero point of the display unit 17 may be balanced in order to thereby compensate for the effects to the earth magnetic field and other stationary stray fields. For performing the searching operation proper, the annular magnet 13 is then placed in the vicinity of the Hall elements 8 and 9, and moved on the skin surface 23. The display deviates from the value set by zero balance as long as the magnetic field of the annular magnet 13 applied at the locus of the Hall elements is directed so as to have at this locus a magnetic field strength vector which is not directed in parallel with the pair of Hall elements.

With a suitable magnetization of the annular magnet 13, the magnetic flux lines thereof in the immediate vicinity of its axis of rotation are linear and parallel to this axis. When the axis of rotation of the annular magnet 13 is positioned approximately normal to the longitudinal axis of the spike 10 in the region of the probe head 7, the output signals of the pair of Hall elements 8 and 9 only re-assume the value set by the zero balancing of the signal processing device 15 when the axis of rotation of the annular magnet 13 and the axis of the hole 11 are aligned with each other with sufficient accuracy. Accordingly, the piercing point of the axis of rotation of the annular magnet 13 through the skin surface 23 of the patient is at the same time the first point 2 to be found. This point may be fixed as the center point of the opening of the annular magnet 13, and marked on the surface of the skin.

In the described procedure, the not completely linear configuration of the magnetic flux lines of the annular magnet 13 outside of its axis of rotation may give rise to an angular error the tangent of which might result in a misdrilling at the locus of the bone, if the drilling jig 4 were adjusted exclusively in accordance with the position of the annular magnet 13 upon reaching the set zero value.

For this reason, the apparatus is provided with a second magnet 16 in the form of a pin-shaped magnetic probe by means of which a second search operation may be performed. To this end, when the puncture incision has been made, the drilling jig 4 is inserted into the anyhow required puncture through the soft tissue surrounding the bone, with the end of this drilling jig remote from the bone being retained with adequate accuracy at the point 2 by the skin incision defined according to the first search operation. Owing to a certain elasticity of the soft tissue, the bone-side end of the drilling jig 4 may be slightly moved in tangential direction on the bone surface.

Now, the magnetic probe 16 is inserted into this drilling jig 4, which probe has its shape conformed to the inner diameter of the drilling jig and is magnetized so as to generate a magnetic field the flux lines of which, in the region of the axis, extend linearly with sufficient exactness, and in parallel with this axis. Principally, the search operation is performed in the same manner as the above described first search operation, whereby the bone-side end of the drilling jig is brought into a sufficiently exact position centrally relative to the considered hole 11 in the spike 10, by slightly moving or displacing this end on the bone surface. In this operation, the end of the drilling jig remote from the bone is held on the previously defined search point 2 with a sufficient degree of accuracy.

In this position of the drilling jig 4, upon removal of the magnetic probe 16 the drilling insert 19 may be inserted, while at the same time removing the Hall probe 6 from the spike 10. Then, the bone 18 may be rough-drilled through the insert 19; subsequently, the insert 19 is removed again, and the cortex of the bone 18 adjacent the drilling jig 4 is drilled out to a larger diameter to receive the bolt shank of the (threaded) bolt 20. The hole formed initially with the use of the insert 19 also in the opposite cortex has its previous diameter unvaried, to receive the threads of the bolt 20. Thereafter, the drill and the drilling jig are removed, and the locking bolts 20 are inserted into the drilled hole.

After to performing the above operations at the distal end, the proximal bolt 24 is to be placed into the corresponding hole (bore) 25, and this operation need not be described in greater detail here since, owing to the small distance to the proximal end of the spike, a conventional location and drilling device as described sub (1) in the introductory part may be used with a sufficient degree of precision for the locating of the proximal holes.

When using the apparatus according to the invention, thus, the usual implantates and the conventional instruments for operation in the proximal region may be used as before. Principally, this applies also to the operations performed in the distal region. For example, the implantate material of the spike 10 and of the bolts 20 may be used in the conventional form, same as the drilling jig 5 and the insert 19. The present location or finding apparatus including the probe 6 and the probe head 7, the two magnets 13 and 16 as well as the signal processing device 15 and the display device 17 may be employed in addition to the conventional instruments. In the conventional instruments, care must only be taken that the drilling jig 4 and the insert 19 are formed of non-magnetic material. This requirement anyhow applies to implantates because of regulations concerning implantate materials.

Supplementarily, it may be noted further that the apparatus is capable of operating effectively even if the probe head cannot be guided by the inner profile of the implantate, such as, for example, in the case of spikes having a circular cross-section. In such instance, auxiliary measures may be taken in order to align or orient the probe head relative to the transverse hole. For example, this may be effected with the aid of a holding device adapted to engage into the hole.

I claim:

1. An apparatus for positioning a drilling jig in axial alignment with at least one predisposed transverse hole in an implanted intramedullary nail, said apparatus comprising at least a first directional element in the form of a magnet (13,16) producing a directional field, and a second directional element in the form of a magnetic field detection device (8,9) with unidirectional reception characteristic; wherein one of said two directional elements is adapted to be aligned with a directional pattern thereof to the axis of the transverse hole (11) to be located, and the other directional element is freely movable; and the output signals of the magnetic field detection device (8,9) are fed, through a signal evaluation and processing device (15), to a display device (17) displaying the relative position of the directional characteristics of said two directional elements to each other.

2. The apparatus according to claim 1, characterized in that at least two freely movable directional elements (13, 16) are provided, which are adapted to be placed to different positions of a body.

3. The apparatus according to claims 1 or 2, characterized in that the magnetic field detection device (8, 9) is adapted to be aligned on the axis of the transverse hole (11) of the implantate (10), and that the magnet (13, 16) is freely movable.

4. The apparatus according to claims 1 or 2, characterized in that the magnet is adapted to be aligned on the axis of the transverse hole, and that the magnetic field detection device is freely movable.

5. The apparatus according to claim 1, characterized in that the first directional element is a permanent magnet (13, 16).

6. The apparatus according to claim 1, characterized in that the first directional element is an electromagnet.

7. The apparatus according to claim 1, characterized in that the magnetic field detection device includes one or more magnetically controllable semiconductor elements (8, 9).

8. The apparatus according to claim 7, characterized in that the magnetic field detection device includes one or more Hall generators (8, 9).

9. The apparatus according to claim 1, characterized in that the magnetic field detection device has the maximum of its detection sensitivity in (on) the axis of its directional characteristic.

10. The apparatus according to claim 1, characterized in that the directive axis of the magnetic field detection device coincides with the minimum of the reception characteristic thereof.

11. An apparatus according to claim 1, characterized in that a pair of Hall generators (8, 9) are positioned in the magnetic field detection device under such angles that their two principal planes intersect each other on the directive axis of the magnetic field detection device.

12. The apparatus according to claim 11, characterized in that said two Hall generators (8, 9) are positioned under right angles to each other.

13. The apparatus according to claim 1, characterized in that an annular magnet (13) serves as the first directional element.

14. The apparatus according to claim 1, characterized in that a magnetic probe (16) adapted to be inserted into a drilling jig (4) serves as the first directional element.

15. The apparatus according to claim 1, characterized in that one of said directional elements (8, 9) is mounted to the head (7) of a probe (6) adapted to be inserted into the implantate (10) having a hollow profile, with the probe head (7) being adapted to be positioned with a reproducible spacing from the accessible end (22) of the implantate (10).

16. The apparatus according to claim 15, characterized in that the probe (16) includes an adjustable stop member (12) allowing for different positioning of the probe head (7).

17. The apparatus according to claim 1, characterized in that the probe head (7) is conformed to the inner profile of the implantate (10) and, with this structure, adapted to be positioned with its directional characteristic coaxially to the transverse hole (11).

18. The apparatus according to claim 1, characterized in that balancing means for the compensation of magnetic stray fields is provided in the signal evaluation device (15).

19. The apparatus according to claim 1, characterized in that the signal evaluation device (15) converts the output signals for presentation on an optical display device (7).

20. The apparatus according to claim 19, characterized in that a conventional monitor may be used as the display device.

21. The apparatus according to claim 1, characterized in that a signalling device alarming the ear or a different human sense organ is provided as said display device.

22. The apparatus according to claim 1, characterized in that the directional field of the magnet (13, 16) is an axially or rotationally symmetrical magnetic field, respectively.

* * * * *